United States Patent [19]

Tsutsumi et al.

[11] 4,425,329
[45] Jan. 10, 1984

[54] WATER-IN-OIL TYPE COSMETIC COMPOSITION

[75] Inventors: Hisao Tsutsumi, Miyashiro; Kazumi Hori, Koganei; Junichi Kawano, Sakura, all of Japan

[73] Assignee: Kao Soap Co., Ltd., Tokyo, Japan

[21] Appl. No.: 181,669

[22] Filed: Aug. 26, 1980

[30] Foreign Application Priority Data

Sep. 7, 1979 [JP] Japan .............................. 54-114792

[51] Int. Cl.³ .................. A61K 7/06; A01N 61/02; A01N 25/00
[52] U.S. Cl. ..................................... 424/70; 424/358; 424/168
[58] Field of Search ......................... 424/358, 70, 168

[56] References Cited

U.S. PATENT DOCUMENTS 4,245,125 1/1981 Wirth et al. .......................... 424/70

FOREIGN PATENT DOCUMENTS 2514873 10/1976 Fed. Rep. of Germany ...... 424/168
4044039 12/1977 Japan ................................... 424/70
649675 12/1928 United Kingdom ................ 424/168
823546 1/1938 United Kingdom ................ 424/168
1000569 2/1952 United Kingdom ................ 424/168

*Primary Examiner*—Delbert R. Phillips
*Attorney, Agent, or Firm*—Oblon, Fisher, Spivak, McClelland & Maier

[57] ABSTRACT

A water-in-oil type cosmetic composition comprising a cosmetic oil base material, water and a specific emulsifier are disclosed. The specific emulsifier comprising the following three components:

(1) 94 to 43% by weight of α-mono(methyl-branched alkyl) glyceryl ether represented by the formula (I):

$$R-OCH_2CH(OH)CH_2OH \qquad (I)$$

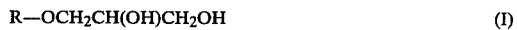

where, R is a methyl-branched saturated hydrocarbon group having 14 to 20 carbon atoms;
(2) 0.4 to 9.8% by weight of a multi-valent metal salt of a saturated or unsaturated aliphatic acid having 10 to 22 carbon atoms; and
(3) 8 to 54% by weight of at least one inorganic or organic salt having a solubility in water of at least 0.2 g per 100 g of water at 20° C.

21 Claims, No Drawings

WATER-IN-OIL TYPE COSMETIC COMPOSITION

BACKGROUND OF THE INVENTION

1. Field of the Invention

The present invention relates to a water-in-oil type cosmetic composition, and, particularly, to a water-in-oil type cosmetic composition containing a large amount of water in a stabilized state.

2. Description of the Prior Art

A water-in-oil type cosmetic composition (hereinafter referred to simply as W/O type cosmetic composition) has a higher resistance against microorganisms than an oil-in-water type cosmetic composition (O/W type cosmetic composition). When applied to the skin, the W/O type cosmetic composition leaves an oil film having a low water permeability, on the surface of the skin, thereby protecting the skin from drying for a long period of time. Further it is unlikely to cause re-emulsification even when contacted with water e.g. by bathing or washings. Thus, the W/O type cosmetic composition has outstanding properties as mentioned above.

However, in the conventional W/O type cosmetic composition, the oil phase is a continuous phase and there is a limitation on the amount of water present in a stabilized state therein. Accordingly, it has the disadvantage that when applied to the skin, it gives an oily and sticky feeling.

Accordingly, the W/O type cosmetic compositions are not widely employed in spite of the fact that they have superior properties as compared with the O/W type cosmetic compositions.

A need therefore continues to exist for a W/O type cosmetic composition which is capable of containing a large amount of water in a stabilized state for a long period of time.

SUMMARY OF THE INVENTION

Accordingly, one object of the present invention is to provide a W/O type cosmetic composition containing a large amount of water in a stabilized state.

A further object is to provide an emulsifier which will allow the preparation of a W/O type cosmetic composition containing a large amount of water in a stabilized state.

Briefly, these objects and other objects of the invention as hereinafter will become more readily apparent can be attained by providing an emulsifier, to be used in the W/O type cosmetic compositions of the present invention, consisting of the following three components:

(1) α-mono(methyl-branched alkyl) glyceryl ether represented by the formula (I):

where, R is a methyl-branched saturated hydrocarbon group having 14 to 20 carbon atoms;

(2) a multi-valent metal salt of a saturated or unsaturated aliphatic acid having 10 to 22 carbon atoms; and (3) one or more inorganic or organic salts having a solubility in water of at least 0.2 g per 100 g of water at 20° C.

DETAILED DESCRIPTION OF THE PREFERRED EMBODIMENTS

It has been found that it is possible to obtain a W/O type cosmetic composition containing a large amount of water in a stabilized state for a long period of time by emulsifying a cosmetic oil base material and water using a certain emulsifier and that it is thereby possible to obtain a W/O type cosmetic composition which gives a good feeling when applied to the skin.

The emulsifier to be used in the W/O type cosmetic composition of the present invention, consists of the following three components:

(1) α-mono(methyl-branched alkyl) glyceryl ether represented by the general formula (I):

(where, R is a methyl-branched saturated hydrocarbon group having 14 to 20 carbon atoms);

(2) a multi-valent metal salt of a saturated or unsaturated aliphatic acid having 10 to 22 carbon atoms; and (3) one or more inorganic or organic salts having a solubility in water of at least 0.2 g per 100 g of water at 20° C.

The methyl-branched alkyl group represented by R- in the formula (I) for the α-mono(methyl-branched alkyl) glyceryl ether of component (1), is preferably the one represented by the following formula (II):

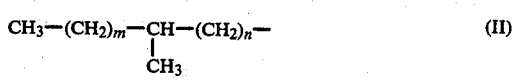

(where, m is an integer of 2 to 14, n is an integer to 3 to 11 and m+n is an integer of 11 to 17). Particularly preferred is the one which contains at least 75% of a methyl-branched alkyl group having 18 carbon atoms and wherein m is 6 to 8.

The compounds represented by the formula (I) are new compounds and may easily be prepared, for instance, by reacting an alkali metal alcoholate of isopropylidene glycerol with R—X (where X is a halogen atom and R has the meaning as defined above) in a normal way and then hydrolyzing 2,3-O-isopropylidene-1-O-methyl-branched alkyl glyceryl ether thus obtained. Preparation of these compounds is disclosed in copending U.S. application Ser. No. 181,659 filed concurrently herewith, the disclosure of which is incorporated herein by reference.

The multi-valent metal salts of aliphatic acids of component (2) may preferably be those having 12 to 18 carbon atoms. And the salts may be, for example, calcium, magnesium, zinc and aluminum salts. Particularly preferred is an aluminum salt. The multi-valent metal salts may be mono-, di- or tri-. However, the mono-salts are particularly preferred.

These multi-valent metal salts of aliphatic acids may be those which have already been synthesized by a double decomposition process or a direct method, or may be prepared during the preparation procedure by carrying out a substitution reaction of a mono-valent salt of an aliphatic acid with a water soluble multi-valent metal salt, such as calcium chloride, magnesium chloride, magnesium sulfate, zinc chloride, aluminum chloride, aluminum sulfate, or alum.

Preferred multi-valent salts of aliphatic acids are aluminum monostearate, aluminum distearate, calcium monostearate, aluminum mono-oleate, aluminum mono-palmitate, and aluminum mono-laurate.

As the inorganic or organic salts of component (3), there may be mentioned alkali metal salts, alkaline earth metal salts or aluminum salts of an inorganic acid such as hydrochloric acid, sulfuric acid, or nitric acid; an oxycarboxylic acid such as citric acid, tartaric acid, lactic acid, or malic acid; a carboxylic acid such as formic acid, acetic acid or sorbic acid; and an aromatic carboxylic acid such as salicylic acid or benzoic acid.

These inorganic or organic salts may be incorporated in the cosmetic composition in a form of a salt, but they may also be prepared by adding, during the preparation of the cosmetic composition, stoichiometric amounts of the corresponding said substances and base substances necessary to form the desired salts.

Preferred inorganic or organic salts may be potassium sulfate, sodium sulfate, magnesium sulfate, aluminum sulfate, potassium nitrate, sodium nitrate, magnesium nitrate, aluminum nitrate, calcium nitrate, potassium chloride, magnesium chloride, sodium chloride, calcium chloride, aluminum chloride, potassium carbonate, sodium carbonate, aluminum carbonate, potassium acetate, sodium acetate, calcium acetate, magensium acetate, sodium formate, potassium formate, magnesium formate, sodium citrate, sodium tartarate, potassium sorbate, sodium sorbate, sodium salicylate, potassium benzoate, and sodium benzoate. Particularly preferred are potassium sulfate, magnesium sulfate, potassium chloride, magnesium chloride, aluminum chloride, sodium citrate, sodium tartarate, potassium sorbate, sodium salicylate and sodium benzoate.

In the W/O type cosmetic composition of the present invention, the emulsifier contains said three components in the weight ratio: 90 to 43% of component (1), 0.4 to 9.8% of component (2) and 8 to 54% of component (3).

The W/O type cosmetic composition of the present invention may contain, in addition to the emulsifier consisting of said components (1) to (3), other cosmetic components of known types, for example, a cosmetic oil base material, a surface active agent as a supplementary emulsifier, a viscosity regulating agent, a medicinal agent, a wetting agent, or an antiseptic agent, as the case requires.

As the cosmetic oil base material, there may be mentioned a hydrocarbon such as squalane, a paraffin oil, or a ceresine oil; a wax such as bees wax, whale wax, or carnauba wax; a natural animal or plant oil or fat such as olive oil, camellia oil, or hydrous lanolin; an aliphatic acid having 10 to 20 carbon atoms, a higher alcohol having 10 to 20 carbon atoms and their esters and silicone oil. As a surface active agent, there may be mentioned a polyoxyethylene alkyl ether, a polyoxyethylene sorbitan aliphatic acid ester, a polyoxyethylene sorbitol aliphatic acid ester, a polyoxyethylene hydrogenated castor oil, a sucrose ester, a sorbitan aliphatic acid ester, a glycerine aliphatic acid ester, an alkali metal salt of an aliphatic acid, an alkylsulfuric acid ester, an alkylphosphoric acid ester, a polyoxyethylene alkylsulfuric acid ester, or a polyoxyethylene alkylphosphoric acid ester. As a viscosity regulating agent, there may be mentioned a synthetic polymer compound such as polyvinylalcohol, a carboxy vinyl polymer, carboxy methyl cellulose, polyvinylpyrrolidone, hydroxy ethyl cellulose, methyl cellulose; a natural rubber such as gelatine, tragacanth gum; and an alcohol such as ethanol, or isopropyl alcohol. As a medicinal agent, there may be mentioned a germicide, an antiphlogistic and a vitamin. As a wetting agent, there may be mentioned propylene glycol, glycerin, 1,3-butylene glycol, sodium pyrrolidone carboxylic acid, and sorbitol. Further, as an antiseptic agent, there may be mentioned methyl parahydroxybenzoate, ethyl para-hydroxybenzoate, propyl para-hydroxybenzoate, butyl para-hydroxybenzoate, benzoic acid, sodium benzoate, sorbic acid, potassium sorbate, and phenoxy ethanol.

A preferred composition of the W/O type cosmetic composition of the present invention is as follows:

|  | Amounts (%) | Preferred Amounts (%) |
|---|---|---|
| Emulsifier consisting of components (1) to (3) | 0.1~10 | 0.5~7 |
| Cosmetic oil base material | 0.1~39.9 | 1~20 |
| Water | 60~99.8 | 80~99 |
| Viscosity regulating agent | 0~10 | 0~2 |
| Surface active agent | 0~10 | 0~5 |
| Medicinal agent | 0~10 |  |
| Wetting agent | 0~30 | 2~10 |
| Antiseptic agent | 0~1 | 0.02~0.5 |
| Stabilizer | 0~10 | 0~10 |

Where the content of the emulsifier is less than 0.1%, it is impossible to stabilize the W/O type emulsion. On the other hand if the content of the emulsifier exceeds 10%, the composition tends to take a gel structure and the creamy viscosity increases to an undesirable extent. Neither condition is desirable for a cosmetic composition. Water may be added in any amount, but should preferably be added in an amount of not less than 60% to obtain a good feeling on use, namely to minimize oily or sticky feelings upon application to the skin.

The W/O type cosmetic composition according to the present invention may be prepared by first emulsifying the above-mentioned ingredients and thereafter stirring the thus-obtained emulsion at a temperature from 5° to 95° C. until it is homogenized.

The W/O type cosmetic composition of the present invention may take any form, for instance, a hand cream, a nutritious cream, cleansing cream, a milky lotion, a cold cream, a hair cream, a vanishing cream, and a foundation cream. Such formulations may be prepared in usual ways.

As described above, the W/O type cosmetic composition of the present invention possesses merits of the conventional W/O type cosmetic compositions and at the same time contains a large amount of water, and thus it is an extremely good cosmetic composition giving little oily or sticky feeling.

Having generally described this invention, a further understanding can be obtained by reference to certain specific examples which are provided herein for purposes of illustration only and are not intended to be limiting unless otherwise specified.

PREPARATORY EXAMPLE 1

In an autoclave having a capacity of 20 liters, 4770 g of isostearic acid isopropyl ester (Emery 2310 isostearic acid isopropyl ester, sold by Emery Industry Inc., U.S.A.) and 239 g of copper-chromium catalyst (made by Nikki) were introduced. Hydrogen gas was added under a pressure of 150 kg/cm$^2$, and the reaction mixture was heated to a temperature of 275° C. The hydrogenation was conducted under a pressure of 150 kg/cm$^2$ at 275° C. for about 7 hours, and thereafter, the reaction product was cooled and the catalyst residue was removed by filtration to obtain 3500 g of a crude product. The crude product was subjected to a distillation under a reduced pressure, whereupon 3300 g of a colourless transparent isostearly alcohol was obtained as a distillate at 80° to 167° C./0.6 mmHg. The isostearyl alcohol (i.e. a methyl-branched stearyl alcohol) thus obtained, had an acid value of 0.05, a saponification value of 5.5, a hydroxyl value of 181.4. It showed IR (liquid film) absorption at 3340 and 1055 cm$^{-1}$, NMR (CCl$_4$ solvent) absorption at δ3.50 (broad triplet, —C$\underline{H}$$_2$—O$\underline{H}$). It has been found by gas chromatography that this alcohol is a mixture of the principal component constituting about 75% of the whole and having a total of 18 carbon atoms in the alkyl group (m plus n equals 15 in the formula II) and the other components having a total of 14 or 16 carbon atoms and that in any case, the branched methyl group is located in the vicinity of the center portion of the main alkyl chain.

PREPARATORY EXAMPLE 2

(i) The isostearyl alcohol obtained by Preparatory Example 1 was introduced in an amount of 2444 g into a reactor having a capacity of 5 liters and equipped with a thermometer, a reflux condenser, a dropping funnel, a nitrogen gas supply line and a stirrer means. Thionyl chloride was dropped from the dropping funnel at room temperature while stirring and supplying nitrogen gas. The reaction mixture generated heat and gas. The temperature of the reaction mixture rose to 31° C. at the initial stage and then gradually dropped to about 18° C. as the amount of thionyl chloride increased. Then, the reaction mixture was heated to a temperature of about 40° C. and thionyl chloride was continued to be dropped. When the generation of the gas weakened, the reaction mixture was heated to 70° to 80° C. and then the generation of the gas become vigorous again and thionyl chloride was continued to be dropped. When the gas generation ceased completely, the addition of thionyl chloride was stopped. The total amount of thionyl chloride added was 2200 g. The reaction product was cooled and then further stirred at 70° to 80° C. for about 1 hour.

The reaction mixture was cooled, and a low boiling point distillate (mainly consisting of unreacted thionyl chloride) was removed at 40° to 50° C. at atmospheric pressure. The residue was cooled with ice, and while stirring, ice cubes were added little by little. After ascertaining that the vigorous gas generation had stopped, either was added and then water was added, and the mixture was thoroughly stirred. The ether layer was separated, neutralized, and after removal of the solvent, subjected to a distillation under a reduced pressure, whereupon 2217 g of isostearyl chloride were obtained from the distillate at 103° to 106° C./0.1 to 1.0 mmHg.

IR (liquid film): 725, 650 cm$^{-1}$
NMR (CCl$_4$): ε3.50 (triplet—CH$_2$Cl)

(ii) 798 g of isopropylidene glycerol, 1500 ml of xylene, 340 g of 93% sodium hydroxide and 300 g of water were fed into a reactor having a capacity of 5 liters and equipped with a thermometer, a stirrer means, a dropping funnel and Dean-Stark trap and heated and refluxed at 130° to 140° C. while stirring. From the water/xylene mixture distilled, water is removed in the Dean-Stark trap and discarded out of the reaction system and the xylene was returned to the reaction system. After about 16 hours of the heating and refluxing, no distillation of water was observed, and at this point, 777 g of the isostearyl chloride prepared in (i) were dropped in a period of about 30 minutes. After the completion of the dropping, the reaction mixture was further heated and refluxed for about 9 hours at 130° to 140° C. to complete the reaction. After cooling, sodium chloride, which precipitated in the reactor, was removed by filtration, and the solvent was removed under a reduced pressure, whereupon 800 g of the distillate at 176° to 206° C./0.25 to 0.60 mmHg were obtained. This was 2,3-O-isopropylidene-1-O-isostearyl glycerykl ether.

IR (liquid film): cm$^{-1}$ 1200 to 1260, 1050 to 1120 (C—O stretching vibration)
NMR (CCl$_4$): δ 3.1 to 4.2

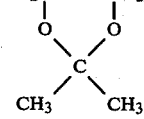

(multiplet, —CH$_2$—O—CH$_2$CH——CH$_2$)

(iii) 1103 g of the isopropylidene isostearyl glyceryl ether obtained in (ii) were fed into a reactor having a capacity of 5 liters and equipped with a stirrer means, a thermometer, and a reflux condenser, and 1500 ml of ethanol and 2000 ml of 0.1 N sulfuric acid were added thereto. The mixture was heated and refluxed at 80° to 85° C. while stirring, and after about 10 hours, it was ascertained by gas chromatography that the hydrolysis of the isopropylidene isostearyl glyceryl ether was completed. After cooling, the mixture was allowed to stand still to separate the oil layer and the water layer. The water layer was extracted with ether, and the extracts were added to the oil layer. An aqueous solution of sodium bicarbonate was added to neutralize the remaining acid. The organic layer was separated, and the solvent was removed under a reduced pressure. Further, heat drying was conducted at 100° C./0.1 mmHg for 3 hours. 900 g of colourless transparent liquid of α-mono(isostearyl) glyceryl ether was obtained.

IR (liquid film): 3400, 1050 to 1140 cm$^{-1}$
NMR (CCl$_4$): ε 3.2 to 3.8

(multiplet, —CH$_2$—O—CH$_2$—CH—CH$_2$—
                                    |     |
                                    OH   OH)

Acid value: 0.08; saponification value: 0.36; Hydroxyl value: 313.8; and Iodine value: 0.32.

EXAMPLE 1

Emulsion Stabilizing Effect

The stability of emulsions was examined with respect to cosmetic bases containing various glyceryl ethers or known emulsifiers (i.e. compounds to be examined) having the following composition.
(Composition)

| Liquid paraffin | 5 (parts by weight) |
| --- | --- |
| Water | 94 |
| Aluminum monostearate | 0.016 |
| Magnesium sulfate | 0.2 |
| Compound to be examined | 0.784 |

(Preparation of the cosmetic bases)

To 5 parts by weight of liquid paraffin, a total of 1 part of aluminum monostearate, magnesium sulfate and the compound to be examined were added, mixed and heated to 70° C. To this mixture, 94 parts by weight of an ion exchanged water at 70° C. were gradually added and emulsified. After the emulsification, the emulsion was cooled down to room temperature while stirring thereby obtaining a cosmetic base. The results are set forth in Table 1.

TABLE 1

|  | Compounds to be examined | Emulsion Types | Immediately after preparation | 7 days later Oil phase separation ratio | 7 days later Water phase separation ratio |
| --- | --- | --- | --- | --- | --- |
| Compounds of the present invention | α-mono(methyl-branched stearyl) glyceryl ether | W/O | Homogeneous cream | 0 | 0 |
|  | α-mono(methyl-branched palmityl) glyceryl ether | W/O | Homogeneous cream | 0 | 0 |
| Comparative compounds | α-mono-oleyl glyceryl ether | W/O | Slightly non-homogeneous cream | 90 | 70 |
|  | α-monostearyl glyceryl ether | W/O | Slightly non-homogeneous cream | 100 | 85 |
|  | 2-hexadecyl-eicosyl α-monoglyceryl ether | — | Separation into oil and water | 100 | 100 |
|  | sorbitan mon-oleate | W/O | Slightly non-homogeneous cream | 54 | 81 |
|  | sorbitan sesqui-oleate | W/O | Slightly non-homogeneous cream | 21 | 36 |
|  | sorbitan monostearate | W/O | Homogeneous cream | 90 | 100 |
|  | glycerin mono-oleate | W/O | Slightly non-homogeneous cream | 15 | 32 |
|  | glycerin monostearate | W/O | Non-homogeneous cream | 100 | 100 |
|  | polyoxyethylene (5) oleyl ether | O/W | Homogeneous cream | 0 | 15 |
|  | polyoxyethylene (7) sorbitol tetraoleate | W/O | Slightly non-homogeneous cream | 26 | 79 |
|  | polyoxyethylene (20) sorbitan monostearate | O/W | Slightly non-homogeneous cream | 0 | 15 |
|  | polyoxyethylene (5) sesquilauryl phosphate | O/W | Slightly non-homogeneous cream | 0 | 21 |
|  | sodium stearylsulfate | O/W | Slightly non-homogeneous cream | 0 | 85 |

$$\text{Oil phase separation ratio} = \frac{\text{Amount of the separated oil phase (ml)}}{6 \text{ (ml)}} \times 100 \text{ (\%)}$$

$$\text{Water phase separation ratio} = \frac{\text{Amount of the separated water (ml)}}{94 \text{ (ml)}} \times 100 \text{ (\%)}$$

As apparent from the above results, it is possible to readily obtain a water-in-oil type cosmetic base containing a large amount of water from the composition containing the component (1) of the present invention and the stability of the emulsion thereby obtained was good. Whereas, with use of other glyceryl ethers or known emulsifiers, it is difficult to obtain a water-in-oil type cosmetic base, and even when a water-in-oil type cosmetic base is formed, it is likely that the water and oil components will soon be separated and it is difficult to obtain a stabilized emulsion.

EXAMPLE 2

The emulsifiers having the compositions shown in Table 2 were prepared, and 1 part of each emulsifier was added to 5 parts by weight of liquid paraffin, and 94 parts by weight of water. Emulsions were prepared in the same manner as in Example 1.

The results of the examination of the stability of the emulsions are shown in Table 3.

TABLE 2

| Emulsifiers |  | α-mono(methyl-branched stearyl) glyceryl ether | Aluminum monostearate | Magnesium sulfate |
| --- | --- | --- | --- | --- |
| Present invention | 1 | 85% | 2% | 13% |
|  | 2 | 70 | 5 | 25 |
|  | 3 | 78 | 8 | 14 |
|  | 4 | 45 | 2 | 53 |
| Comparative emulsions | 5 | 100 | 0 | 0 |
|  | 6 | 95 | 5 | 0 |
|  | 7 | 85 | 0 | 15 |
|  | 8 | 50 | 50 | 0 |
|  | 9 | 70 | 0 | 30 |
|  | 10 | 50 | 30 | 20 |
|  | 11 | 30 | 20 | 50 |
|  | 12 | 0 | 50 | 50 |
|  | 13 | 0 | 100 | 0 |
|  | 14 | 0 | 0 | 100 |

TABLE 3

| Emulsifiers |  | Emulsion Types | Immediately after preparation | 7 days later Oil phase separation ratio | 7 days later Water phase separation ratio |
| --- | --- | --- | --- | --- | --- |
| Present invention | 1 | W/O | Homogeneous cream | 0 | 0 |
|  | 2 | " | Homogeneous cream | 0 | 0 |
|  | 3 | " | Homogeneous cream | 0 | 0 |
|  | 4 | " | Homogeneous cream | 0 | 0 |
| Comparative emulsions | 5 | " | Homogeneous milky lotion | 15 | 0 |
|  | 6 | " | Homogeneous cream | 13 | 0 |
|  | 7 | " | Homogeneous cream | 12 | 0 |
|  | 8 | " | Non-homogeneous cream | 75 | 29 |
|  | 9 | " | Non-homogeneous cream | 100 | 15 |
|  | 10 | " | Homogeneous cream | 7 | 11 |
|  | 11 | " | Homogeneous cream | 15 | 5 |
|  | 12 | " | Gel | 100 | 93 |
|  | 13 | " | Gel | 100 | 75 |
|  | 14 | — | Not emulsified | 100 | 100 |

It is apparent from the above results that it is necessary to incorporate the three components (1), (2) and (3)

in the emulsifier to obtain a stabilized W/O type emulsion, and that if the proportions of the three components are outside of the specified limits, the emulsion state may be good only for a short period of time immediately after the preparation and is likely to become unstable as time passes.

EXAMPLE 3

Feeling tests were conducted by a panel of 10 specialists with respect to the water-in-oil type cosmetic compositions of the present invention and the comparative products. At the same time, the stability of emulsions after one month was examined.

The standards for evaluation of the feeling tests and the stability of emulsions are as listed below, and the results obtained are shown in Table 4.

(Standards for evaluation of the feeling tests)

| Strong | +2 |
|---|---|
| Moderate | +1 |
| Normal | 0 |
| None | −1 |
| Absolutely none | −2 |

(Standards for determination of the stability of emulsions)

| | |
|---|---|
| O | No separation or creaming occurs after being left for one month at a room temperature |
| Δ | Creaming slightly observed after being left for one month at a room temperature |
| x | Separation observed after being left for one month at a room temperature |

TABLE 4

| | Present invention | | Comparative products | | |
|---|---|---|---|---|---|
| | 1 | 2 | 3 | 4 | 5 |
| α-mono(methyl-branched stearyl) glyceryl ether | 1.8 | 1.8 | | | |
| Aluminum monostearate | 0.04 | 0.04 | 0.04 | | |
| Magnesium sulfate | 0.5 | 0.5 | | | |
| Lanoline alcohol | | | 2.30 | | |
| Glycerine mono-oleate | | | | 2.34 | 2.34 |
| Isopropyl myristate | 2 | 15 | 15 | 15 | 30 |
| Liquid paraffin | 4 | 20 | 20 | 20 | 20 |
| Running water | 91.66 | 62.66 | 62.66 | 47.66 | 47.66 |
| Propylene glycol | | | | 15 | |
| Stability of emulsions | O | O | X | Δ | O |
| Feelings Sticky feeling | −1.8 | −1.0 | −1.3 | +1.4 | +1.8 |
| Oily feeling | −1.3 | −1.3 | −1.2 | +0.3 | +1.7 |

EXAMPLE 4

Nutrient Cream (Composition)

| | | |
|---|---|---|
| (1) α-mono(methyl-branched stearyl) glyceryl ether | | 2.0% |
| (2) aluminum monostearate | | 0.04 |
| (3) potassium sulfate | | 0.5 |
| (4) squalane | | 4.0 |
| (5) liquid paraffin | | 2.0 |
| (6) hexadecyl-2-ethyl hexanoate | | 2.0 |
| (7) sodium benzoate | | 0.3 |
| (8) propylene glycol | | 2.0 |
| (9) acetic acid dl-α-tocopherol | | 0.1 |
| (10) perfume | | 0.1 |
| (11) purified water | | the rest |

(Method for preparation)

Components (1) to (6) were mixed and heated to 75° C. To this mixture a mixture of components (7), (8) and (11) heated at 70° C. was added while stirring thereby emulsifying the mixture. After the emulsification, the mixture thus obtained was cooled down to 60° C. and then components (9) and (10) were added, and then the whole mixture was further cooled to room temperature thereby obtaining a final product.

The nutrient cream thus prepared has a good stability and gives a good feeling upon application to the skin, i.e. the results of the feeling tests (in the same manner as in Example 3) indicated the evaluated values to be −1.4 for sticky feeling and −1.2 for oily feeling.

EXAMPLE 5

Hand Cream (W/O type)

(Composition)

| | |
|---|---|
| (1) α-mono(methyl-branched palmityl) glyceryl ether | 1.5% |
| (2) calcium monostearate | 0.02 |
| (3) aluminum chloride | 0.8 |
| (4) IPM (isopropyl myristate) | 4.5 |
| (5) dimethyl polysiloxane | 4.0 |
| (6) methyl para-hydroxy benzoate | 0.2 |
| (7) sorbitol | 10.0 |
| (8) purified water | the rest |

(Method for preparation)

Components (1) to (5) were mixed and heated to 75° C. To this mixture, a mixture of components (6) to (8) heated at 75° C. was gradually added while stirring thereby emulsifying the mixture. The whole mixture was cooled down to room temperature thereby obtaining the final product.

The hand cream thus prepared has a good emulsion stability for a long period of time and gives a good feeling upon application (i.e. sticky feeling being −1.7, and oily feeing being −0.9 according to the feeling tests conducted in the same manner as in Example 3). It further has a water repellent property and shows superior characteristics as a hand cream.

EXAMPLE 6

Cold Cream (W/O type)

(Composition)

| | |
|---|---|
| (1) α-mono(methyl-branched stearyl) glyceryl ether | 5.5% |
| (2) aluminum distearate | 0.05 |
| (3) sodium nitrate | 1.0 |
| (4) liquid paraffin | 10.0 |
| (5) oleyl alcohol | 1.0 |
| (6) potassium sorbate | 0.2 |
| (7) glycerine | 5.0 |
| (8) perfume | 0.1 |
| (9) purified water | the rest |

(Method for preparation)

Components (1) to (5) were mixed and heated to 75° C. To the mixture, a mixture of components (6), (7) and (9) heated at 75° C. was gradually added while stirring thereby emulsifying the mixture. After cooling, component (8) was added to obtain the final product.

EXAMPLE 7

Vanishing Cream (W/O type)

(Composition)

| | | |
|---|---|---|
| (1) | α-mono(methyl-branched stearyl) glyceryl ether | 2.0% |
| (2) | aluminum monostearate | 0.2 |
| (3) | calcium chloride | 0.4 |
| (4) | stearic acid | 1.0 |
| (5) | glycerol tri-2-ethylhexanoate | 7.0 |
| (6) | propyl para-hydroxy benzoate | 0.2 |
| (7) | sorbitol | 5.0 |
| (8) | perfume | 0.2 |
| (9) | purified water | the rest |

(Method for preparation)

Components (1) to (6) were mixed and heated to 75° C. To this mixture, a mixture of components (7) and (9) heated at 75° C. was gradually added while stirring thereby emulsifying the mixture. After cooling, component (8) is added thereby obtaining the final product.

The vanishing cream thus prepared has a good emulsion stability for a long period of time and gives a good feeling upon application, i.e. the evaluation by the feeling tests being −1.1 for sticky feeling and −0.7 for oily feeling (in the same manner as in Example 3).

EXAMPLE 8

Milky Lotion (W/O type)

(Composition)

| | | |
|---|---|---|
| (1) | α-mono(methyl-branched stearyl) glyceryl ether | 2.0% |
| (2) | aluminum mono-laurate | 0.08 |
| (3) | sodium tartarate | 1.5 |
| (4) | sorbitan sesqui-oleate | 2.0 |
| (5) | stearic acid | 1.5 |
| (6) | olive oil | 4.0 |
| (7) | liquid paraffin | 4.0 |
| (8) | dibutyl hydroxy toluene | 0.02 |
| (9) | propyl para-hydroxy benzoate | 0.2 |
| (10) | carboxy methyl cellulose | 0.1 |
| (11) | 1,3-butylene glycol | 5.0 |
| (12) | perfume | 0.2 |
| (13) | ion-exchanged water | the rest |

(Method for preparation)

Components (1) to (9) were mixed and heated to 75° C. To this mixture, a mixture of components (10), (11) and (13) heated at 75° C. was added while stirring thereby emulsifying the mixture. After cooling, component (12) was added to obtain a final product.

The milky lotion thus prepared had a good emulsion stability and gives a good feeling upon application, i.e. the evaluation by the feeling tests being −1.2 for sticky feeling and −0.9 for oily feeling (in the same manner as in Example 3).

EXAMPLE 9

Hair Cream (W/0 type)

(Composition)

| | | |
|---|---|---|
| (1) | α-mono(methyl-branched stearyl) glyceryl ether | 2.0% |

-continued

| | | |
|---|---|---|
| (2) | calcium mono-oleate | 0.06 |
| (3) | sodium salicylate | 0.7 |
| (4) | liquid paraffin | 10.0 |
| (5) | glycerin | 10.0 |
| (6) | perfume | 0.1 |
| (7) | water | the rest |

(Method for preparation)

Components (1) to (4) were mixed and heated to 75° C. To this mixture, a mixture of components (5) and (7) heated at 75° C. was gradually added while stirring thereby emulsifying the mixture. After cooling, component (6) was added to obtain a final product.

EXAMPLE 10

Foundation Cream (W/O type)

(Composition)

| | | |
|---|---|---|
| (1) | α-mono(methyl-branched stearyl) glyceryl ether | 2.0% |
| (2) | aluminum monostearate | 0.02 |
| (3) | potassium sorbate | 0.05 |
| (4) | magnesium sulfate | 1.0 |
| (5) | polyoxyethylene (7) sorbitol tetra-oleate | 3.5 |
| (6) | liquid paraffin | 8.5 |
| (7) | bleached bees wax | 1.0 |
| (8) | talc | 6.0 |
| (9) | kaolin | 8.0 |
| (10) | titanium oxide | 1.0 |
| (11) | iron oxide | 0.5 |
| (12) | glycerin | 8.0 |
| (13) | perfume | 0.05 |
| (14) | water | the rest |

(Method for preparation)

Components (1) to (6) were mixed and heated to 75° C. To this mixture, a mixture of components (12) and (14) heated at 75° C. was gradually added while stirring thereby emulsifying the mixture. Then, components (8) to (11) were added and homogeneously kneaded. After cooling, component (13) was added to obtain a final product.

The foundation cream thus prepared had a good emulsion stability for a long period of time and gives a good feeling upon application, giving little sticky feeling (−0.8) or oily feeling (−1.1).

Having now fully described this invention, it will be apparent to one of ordinary skill in the art that many changes and modifications can be made thereto without departing from the spirit or scope of the invention set forth herein.

What is claimed as new and desired to be secured by Letters Patent of the United States is:

1. A water-in-oil type cosmetic composition which comprises:
   (A) a cosmetic oil base material;
   (B) water; and
   (C) an emulsifier comprising the following three components:
      (1) 94 to 43% by weight of α-mono(methyl-branched alkyl) glyceryl ether represented by the formula (I):

$$R-OCH_2CH(OH)CH_2OH \qquad (I)$$

where, R is a methyl-branched saturated hydrocarbon group having 14 to 20 carbon atoms;

(2) 0.4 to 9.8% by weight of a multi-valent metal salt of a saturated or unsaturated aliphatic acid having 10 to 22 carbon atoms; and (3) 8 to 54% by weight of at least one inorganic or organic salt having a solubility in water of at least 0.2 g per 100 g of water at 20° C.

2. The water-in-oil type cosmetic composition as claimed in claim 1, wherein the emulsifier (C) constitutes 0.1 to 10% by weight of the whole composition.

3. The water-in-oil type cosmetic composition as claimed in claim 1, wherein the methyl-branched alkyl group represented by R in α-mono(methyl-branched alkyl) glyceryl ether of component (1) is represented by the formula (II):

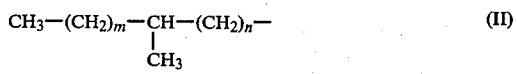
(II)

where, m is an integer of 2 to 14, n is an integer of 3 to 11, and the total of m+n is 11 to 17.

4. The water-in-oil type cosmetic composition as claimed in claim 1, wherein the multi-valent metal of the multi-valent metal salt of an aliphatic acid of component (2) is selected from the group consisting of calcium, magnesium, zinc and aluminum.

5. The water-in-oil type cosmetic composition as claimed in claim 4, wherein the multi-valent metal salt of an aliphatic acid of component (2) is an aluminum salt.

6. The water-in-oil type cosmetic composition as claimed in claim 4, wherein the multi-valent metal salt of an aliphatic acid of component (2) is selected from the group consisting of aluminum monostearate, aluminum di-stearate, calcium monostearate, aluminum mono-oleate, aluminum mon-palmitate, and aluminum mono-laurate.

7. The water-in-oil type cosmetic composition as claimed in claim 1, wherein the inorganic or organic salt of component (3) is an inorganic salt.

8. The water-in-oil type cosmetic composition as claimed in claim 7, wherein the inorganic salt is selected from the group consisting of sulfate, chloride nitrate and carbonate.

9. The water-in-oil type cosmetic composition as claimed in claim 7, wherein the inorganic salt is selected from the group consisting of potassium sulfate, magnesium sulfate, potassium chloride, magnesium chloride and aluminum chloride.

10. The water-in-oil type cosmetic composition as claimed in claim 1, wherein the inorganic or organic salt of component (3) is an organic salt.

11. The water-in-oil type cosmetic composition as claimed in claim 10, wherein the organic salt is selected from the group consisting of potassium acetate, sodium acetate, calcium acetate, magnesium acetate, potassium formate, sodium formate, magnesium formate, sodium citrate, sodium tartrate, potassium sorbate, sodium sorbate, sodium salicylate, potassium benzoate, and sodium benzoate.

12. An emulsifier composition comprising the following three components:

(1) 94 to 43% by weight of α-mono(methyl-branched alkyl) glyceryl ether represented by the formula (I):

(I)

where, R is a methyl-branched saturated hydrocarbon group having 14 to 20 carbon atoms;

(2) 0.4 to 9.8% by weight of a multi-valent metal salt of a saturated or unsaturated aliphatic acid having 10 to 22 carbon atoms; and (3) 8 to 54% by weight of at least one inorganic or organic salt having a solubility in water of at least 0.2 g per 100 g of water at 20° C.

13. The emulsifier composition as claimed in claim 12, wherein the methyl-branched alkyl group represented by R in α-mono(methyl-branched alkyl) glyceryl ether of component (1) is represented by the formula (II):

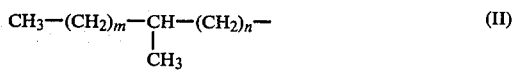
(II)

where, m is an integer of 2 to 14, n is an integer of 3 to 11, and the total of m+n is 11 to 17.

14. The emulsifier composition as claimed in claim 12, wherein the multi-valent metal of the multi-valent metal salt of an aliphatic acid of component (2) is selected from the group consisting of calcium, magnesium, zinc and aluminum.

15. The emulsifier composition as claimed in claim 14, wherein the multi-valent metal salt of an aliphatic acid of component (2) is an aluminum salt.

16. The emulsifier composition as claimed in claim 14, wherein the multi-valent metal salt of an aliphatic acid of component (2) is selected from the group consisting of aluminum monostearate, aluminum di-stearate, calcium monostearate, aluminum mono-oleate, aluminum mono-palmitate and aluminum mono-laurate.

17. The emulsifier composition as claimed in claim 12, wherein the inorganic or organic salt of component (3) is an inorganic salt.

18. The emulsifier composition as claimed in claim 17, wherein the inorganic salt is selected from the group consisting of sulfate, chloride, nitrate and carbonate.

19. The emulsifier composition as claimed in claim 17, wherein the inorganic salt is selected from the group consisting of potassium sulfate, magnesium sulfate, potassium chloride, magnesium chloride and aluminum chloride.

20. The emulsifier composition as claimed in claim 12, wherein the inorganic or organic salt of component (3) is an organic salt.

21. The emulsifier composition as claimed in claim 20, wherein the organic salt is selected from the group consisting of potassium acetate, sodium acetate, calcium acetate, magnesium acetate, potassium formate, sodium formate, magnesium formate, sodium citrate, sodium tartrate, potassium sorbate, sodium sorbate, sodium salicylate, potassium benzoate, and sodium benzoate.

* * * * *